United States Patent
Zhang et al.

(12) 
(10) Patent No.: US 6,544,996 B2
(45) Date of Patent: *Apr. 8, 2003

(54) 1-PHENYL-4-(1-[2-ARYL]CYCLOPROPYL) METHYLPIPERAZINES: DOPAMINE RECEPTOR LIGANDS

(75) Inventors: Xiaoyan Zhang, Belle Meade, NJ (US); Jennifer Tran, Guilford, CT (US); He Zhao, Branford, CT (US); Andrew Thurkauf, Danbury, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/942,369

(22) Filed: Aug. 29, 2001

(65) Prior Publication Data

US 2002/0022630 A1 Feb. 21, 2002

Related U.S. Application Data

(63) Continuation of application No. 09/478,718, filed on Jan. 6, 2000, now Pat. No. 6,284,761.
(60) Provisional application No. 60/115,161, filed on Jan. 8, 1999.

(51) Int. Cl.$^7$ .................. A61K 31/495; A61P 25/18; C07D 295/33
(52) U.S. Cl. .................. 514/255.03; 546/392; 546/394
(58) Field of Search ..................... 514/255.03

(56) References Cited

U.S. PATENT DOCUMENTS 6,284,761 B1 * 11/2001 Zhang et al. .......... 514/255.03

FOREIGN PATENT DOCUMENTS

| EP | 0 188 887 A | 7/1986 |
| EP | 0 755 923 A | 1/1997 |
| WO | WO 96 16040 A | 5/1996 |
| WO | WO 98 33784 A | 8/1998 |

OTHER PUBLICATIONS

Glickstein et al., Pharmacology & Therapeutics 91:63–83, 2001.*

* cited by examiner

Primary Examiner—Venkataraman Balasubramanian
(74) Attorney, Agent, or Firm—McDonnell Boehnen Hulbert & Berghoff

(57) ABSTRACT

Disclosed are compounds of the formula:

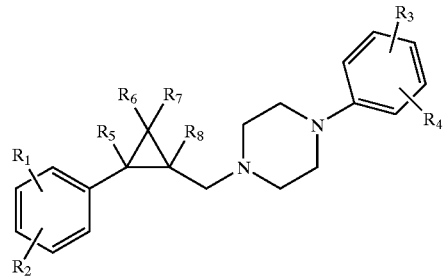

or pharmaceutically acceptable addition salts thereof wherein:

$R_1$, $R_2$, $R_3$, $R_4$ and $R_5$, $R_6$, $R_7$, and $R_8$ represent organic and/or inorganic substituents as defined herein, which compounds are useful for the treatment and/or prevention of neuropsychological disorders including, but not limited to, schizophrenia, mania, dementia, depression, anxiety, compulsive behavior, substance abuse, Parkinson-like motor disorders and motion disorders related to the use of neuroleptic agents.

22 Claims, No Drawings

1-PHENYL-4-(1-[2-ARYL]CYCLOPROPYL) METHYLPIPERAZINES: DOPAMINE RECEPTOR LIGANDS

This application is a continuation of application Ser. No. 09/478,718, filed Jan. 6, 2000, now U.S. Pat. No. 6,284,761 B1, which claims benefit of priority from U.S. Provisional application No. 60/115,161 filed Jan. 8, 1999.

BACKGROUND OF THE INVENTION

1. Field of the Invention

This invention relates to 1-phenyl-4-(1-[2-aryl]cyclopropyl)methylpiperazine derivatives and to pharmaceutical compositions containing such compounds. It also relates to the use of such compounds in the treatment or prevention of psychotic disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has recently been identified (Nature, 350: 610 (Van Tol et al., 1991); Nature, 347: 146 (Sokoloff et al., 1990)). Its unique localization in limbic brain areas and its differential recognition of various antipsychotics indicates that the $D_4$ receptor plays a major role in the etiology of schizophrenia. Selective $D_4$ antagonists are considered effective antipsychotics free from the neurological side effects displayed by conventional neuroleptics.

SUMMARY OF THE INVENTION

This invention provides novel compounds of Formula I which interact with dopamine subtypes. Accordingly, a first aspect of the invention is directed to a compound of Formula I:

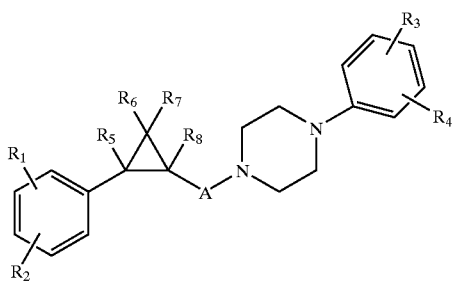

wherein:

$R_1$ and $R_2$ are the same or different and represent hydrogen, halogen, $C_1$–$C_6$ alkyl, $C_1$–$C_6$ alkoxy, $C_1$–$C_6$ alkylthio, hydroxy, amino, mono- or di($C_1$–$C_6$) alkylamino, cyano, nitro, perfluoro($C_1$–$C_6$)alkyl or perfluoro($C_1$–$C_6$)alkoxy;

$R_3$ and $R_4$ are the same or different and represent hydrogen, halogen, $C_1$–$C_6$ alkyl, $C_1$–$C_6$ alkoxy, $C_1$–$C_6$ alkylthio, hydroxy, amino, mono- or di($C_1$–$C_6$) alkylamino, cyano, nitro, perfluoro($C_1$–$C_6$)alkyl or perfluoro($C_1$–$C_6$)alkoxy;

A is an alkylene group of 1–3 carbon atoms; and $R_5$, $R_6$, $R_7$, and $R_8$ are the same or different and represent hydrogen or $C_1$–$C_6$ alkyl.

Dopamine $D_4$ receptors are concentrated in the limbic system (Science, 265: 1034 (Taubes, 1994)) which controls cognition and emotion. Therefore, compounds that interact with these receptors are useful in the treatment of cognitive disorders. Such disorders include cognitive deficits which are a significant component of the negative symptoms (social withdrawal and unresponsiveness) of schizophrenia. Other disorders include those involving memory impairment or attention deficit disorders.

Compounds of the present invention demonstrate high affinity and selectivity in binding to the $D_4$ receptor subtype. These compounds are therefore useful in treatment of a variety of neuropsychological disorders, such as, for example, schizophrenia, psychotic depression and mania. Other dopamine-mediated diseases such as Parkinsonism and tardive dyskinesias can also be treated directly or indirectly by modulation of $D_4$ receptors.

Compounds of this invention are also useful in the treatment of depression, memory-impairment or Alzheimer's disease by modulation of $D_4$ receptors since they exist selectively in areas known to control emotion and cognitive functions.

Thus, in another aspect, the invention provides methods for treatment and/or prevention of neuropsychological or affective disorders including, for example, schizophrenia, mania, dementia, depression, anxiety, compulsive behavior, substance abuse, memory impairment, cognitive deficits, Parkinson-like motor disorders, e.g., Parkinsonism and dystonia, and motion disorders related to the use of neuroleptic agents. In addition, the compounds of the invention are useful in treatment of depression, memory-impairment or Alzheimer's disease. Further, the compounds of the present invention are useful for the treatment of other disorders that respond to dopaminergic blockade, e.g., substance abuse and obsessive compulsive disorder. These compounds are also useful in treating the extrapyramidal side effects associated with the use of conventional neuroleptic agents.

Additionally, when appropriately labeled, compounds of this invention are useful as probes for the localization of dopamine receptors. Localization of receptors may be performed in vitro, e.g., via autoradiography of tissue sections, or in vivo, e.g., via positron emission tomography (PET).

In yet another aspect, the invention provides pharmaceutical compositions comprising compounds of Formula I.

In another aspect, the invention provides intermediates useful in the preparation of compounds of Formula I.

The invention also provides methods for preparing the compounds of the invention.

DETAILED DESCRIPTION OF THE INVENTION

The invention encompasses the compounds of Formula I described above.

Preferred compounds of Formula I are those where $R_5$, $R_6$, $R_7$, and $R_8$ are $C_1$–$C_3$ alkyl, and more preferably, hydrogen or methyl. Even more preferred compounds of Formula I are those where $R_5$, $R_6$, $R_7$ and $R_8$ are hydrogen. In the more preferred compounds of Formula I the hydrogens at positions $R_5$ and $R_8$ are in a trans configuration to one another. Particularly preferred compounds of Formula I have $R_1$, $R_2$, $R_3$ and $R_4$ as hydrogen, halogen or lower alkyl.

In other preferred compounds of I, when $R_1$ and $R_3$–$R_8$ are all hydrogen, $R_2$ is not tert-butyl, or more preferably not $C_1$–$C_6$ alkyl.

In addition, the invention encompasses compounds of Formula II.

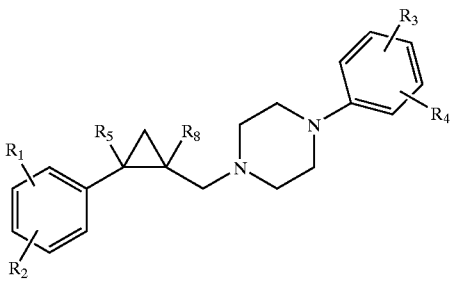

$R_1$ and $R_2$ are the same or different and represent hydrogen, halogen, $C_1$–$C_6$ alkyl, $C_1$–$C_6$ alkoxy, $C_1$–$C_4$ alkylthio, hydroxy, amino, mono- or di($C_1$–$C_6$) alkylamino, cyano, nitro, perfluoro($C_1$–$C_6$)alkyl or perfluoro($C_1$–$C_6$)alkoxy;

$R_3$ and $R_4$ are the same or different and represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$) alkylamino, cyano, nitro, perfluoro($C_1$–$C_6$)alkyl or perfluoro($C_1$–$C_6$)alkoxy; and $R_5$, $R_6$, $R_7$, and $R_8$ are the same or different and represent hydrogen or $C_1$–$C_3$ alkyl;

provided that $R_2$ is not t-butyl when $R_1$ and $R_3$–$R_8$ are all hydrogen.

In preferred compounds of Formula II, $R_5$ and $R_8$ are trans to each other. In yet more preferred compounds of Formula II, $R_5$, $R_6$, $R_7$, and $R_8$ are hydrogen or methyl. More preferred compounds of Formula II are those where $R_5$, $R_6$, $R_7$ and $R_8$ are hydrogen. In the most preferred compounds of Formula I the hydrogens at positions $R_5$ and $R_8$ are in a trans configuration to one another. Particularly preferred compounds of Formula I have $R_1$, $R_2$, $R_3$ and $R_4$ as hydrogen, halogen or lower alkyl.

In other preferred compounds of Formula I, one of $R_1$ and $R_2$ may be halogen, preferably in the para position on the phenyl ring, while the other is hydrogen. In these preferred compounds $R_3$ and $R_4$ are preferably in the para and one of the ortho, i.e., the 4 and 2) positions with respect to the point of attachment to the phenyl ring and are hydrogen, halogen or $C_1$–$C_3$ alkyl, provided that at least one of $R_3$ and $R_4$ is not hydrogen.

In addition, the invention encompasses compounds of Formula III:

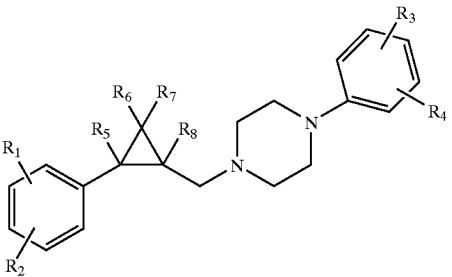

wherein $R_1$ and $R_2$ independently represent hydrogen, halogen, $C_1$–$C_3$ alkyl, $C_1$–$C_4$ alkoxy, $C_1$–$C_4$ alkylthio, hydroxy, amino, mono- or di($C_1$–$C_6$)alkylamino, cyano, nitro, perfluoro($C_1$–$C_6$)alkyl or perfluoro($C_1$–$C_6$)alkoxy;

$R_3$ and $R_4$ are the same or different and represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$) alkylamino, cyano, nitro, perfluoro($C_1$–$C_6$)alkyl or perfluoro($C_1$–$C_6$)alkoxy; and $R_5$, $R_6$, $R_7$, and $R_8$ are the same or different and represent hydrogen or $C_1$–$C_3$ alkyl.

Preferred compounds of Formula III are those where $R_1$ and $R_2$ are independently hydrogen, halogen, methyl, or ethyl. In more preferred compounds of Formula III, $R_1$ and $R_2$ are both hydrogen.

In other preferred compounds of Formula III, at least one of $R_1$ and $R_2$ is not hydrogen. In more preferred compounds of Formula III, at least one of $R_1$ and $R_2$ is not hydrogen, i.e., it is selected from halogen, $C_1$–$C_3$ alkyl, $C_1$–$C_4$ alkoxy, $C_1$–$C_4$ alkylthio, hydroxy, amino, mono- or di($C_1$–$C_6$) alkylamino, cyano, nitro, perfluoro($C_1$–$C_6$)alkyl and perfluoro($C_1$–$C_6$)alkoxy, and $R_3$ and $R_4$ are in the 2 and 4 positions on the phenyl group. In these more preferred compounds of Formula III, $R_5$, $R_6$, $R_7$, and $R_8$ are hydrogen or methyl. Further, in these more preferred compounds of Formula III, $R_5$ and $R_8$ are trans to each other.

In addition, the invention encompasses compounds of Formula IV:

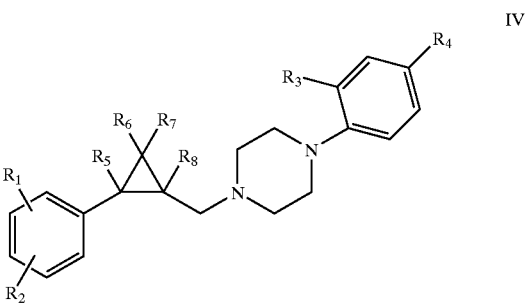

$R_1$ and $R_2$ independently represent hydrogen, halogen, $C_1$–$C_6$ alkyl, $C_1$–$C_6$ alkoxy, $C_1$–$C_4$ alkylthio, hydroxy, amino, mono- or di($C_1$–$C_6$)alkylamino, cyano, nitro, perfluoro($C_1$–$C_6$)alkyl or perfluoro($C_1$–$C_6$)alkoxy;

$R_3$ and $R_4$ are the same or different and represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$) alkylamino, cyano, nitro, perfluoro($C_1$–$C_6$)alkyl or perfluoro($C_1$–$C_6$)alkoxy; and $R_5$, $R_6$, $R_7$, and $R_8$ are the same or different and represent hydrogen or $C_1$–$C_3$ alkyl.

Preferred compounds of Formula IV are those where $R_1$ and $R_2$ independently represent hydrogen, halogen, $C_1$–$C_6$ alkoxy, $C_1$–$C_4$ alkylthio, hydroxy, amino, mono- or di($C_1$–$C_6$)alkylamino, cyano, nitro or perfluoro($C_1$–$C_6$) alkoxy. More preferred compounds of Formula IV are those where $R_5$, $R_6$, $R_7$, and $R_8$ are hydrogen or methyl. In the preferred compounds of Formula IV, $R_5$ and $R_8$ are trans to each other.

Other more preferred compounds of Formula IV are those where $R_3$ is hydrogen, halogen, $C_1$–$C_3$ alkyl, or $C_1$–$C_3$ alkoxy. Particularly preferred compounds of Formula IV are those where $R_4$ is hydrogen, halogen, $C_1$–$C_3$ alkyl, or $C_1$–$C_3$ alkoxy and $R_3$ is hydrogen, halogen, $C_1$–$C_3$ alkyl, or $C_1$–$C_3$ alkoxy.

Other preferred compounds of Formula IV are those where $R_3$ represents hydrogen, chloro, or methyl. Still other preferred compounds of Formula IV are those where $R_4$ represents hydrogen, bromo chloro, methyl, nitro, or amino.

Particularly preferred compounds of Formula IV are those wherein $R_3$ represents hydrogen, chloro, or methyl, and $R_4$ represents hydrogen, bromo chloro, methyl, nitro, or amino.

In addition, the invention encompasses compounds of Formula V:

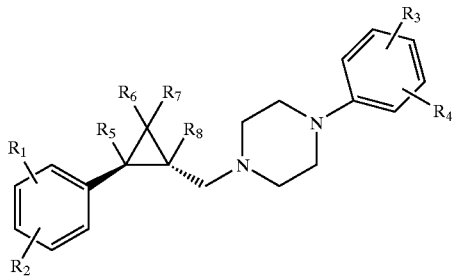

Va wherein $R_1$ and $R_2$ independently represent hydrogen, halogen, $C_1$–$C_6$ alkyl, $C_1$–$C_6$ alkoxy, $C_1$–$C_4$ alkylthio, hydroxy, amino, mono- or di($C_1$–$C_6$)alkylamino, cyano, nitro, perfluoro($C_1$–$C_6$)alkyl or perfluoro($C_1$–$C_6$)alkoxy;

$R_3$ and $R_4$ are the same or different and represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$) alkylamino, cyano, nitro, perfluoro($C_1$–$C_6$)alkyl or perfluoro($C_1$–$C_6$)alkoxy; and $R_5$, $R_6$, $R_7$, and $R_8$ are the same or different and represent hydrogen or $C_1$–$C_3$ alkyl.

Preferred compounds of Formula Va are those where $R_1$ and $R_2$ independently represent hydrogen, halogen, $C_1$–$C_6$ alkoxy, $C_1$–$C_4$ alkylthio, hydroxy, amino, mono- or di($C_1$–$C_6$)alkylamino, cyano, nitro or perfluoro($C_1$–$C_6$) alkoxy. More preferred compounds of Formula Va are those where $R_5$, $R_6$, $R_7$, and $R_8$ are hydrogen or methyl. In the preferred compounds of Formula Va, $R_5$ and $R_8$ are trans to each other.

Other more preferred compounds of Formula Va are those where $R_3$ is hydrogen, halogen, $C_1$–$C_3$ alkyl, or $C_1$–$C_3$ alkoxy. Particularly preferred compounds of Formula Va are those where $R_4$ is hydrogen, halogen, $C_1$–$C_3$ alkyl, or $C_1$–$C_3$ alkoxy and $R_3$ is hydrogen, halogen, $C_1$–$C_3$ alkyl, or $C_1$–$C_3$ alkoxy.

Other preferred compounds of Formula Va are those where $R_3$ represents hydrogen, chloro, or methyl. Still other preferred compounds of Formula Va are those where $R_4$ represents hydrogen, bromo chloro, methyl, nitro, or amino. Particularly preferred compounds of Formula Va are those wherein $R_3$ represents hydrogen, chloro, or methyl, and $R_4$ represents hydrogen, bromo chloro, methyl, nitro, or amino.

In still other preferred compounds of Formula Va, one of $R_1$ and $R_2$ may be halogen, preferably in the para position on the phenyl ring, while the other is hydrogen. In these preferred compounds $R_3$ and $R_4$ are preferably in the para and one of the ortho, i.e., the 4 and 2) positions with respect to the point of attachment to the phenyl ring and are hydrogen, halogen or $C_1$–$C_3$ alkyl, provided that at least one of $R_3$ and $R_4$ is not hydrogen.

Particularly preferred compounds of the invention are those having a skeleton with the following stereochemical configuration:

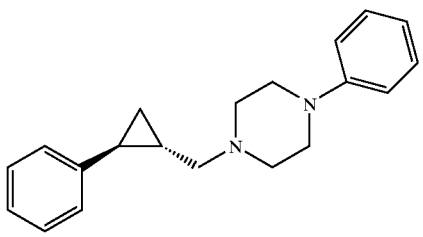

Such compounds are encompassed within Formula Va.

In addition, the invention encompasses compounds of Formula Vb:

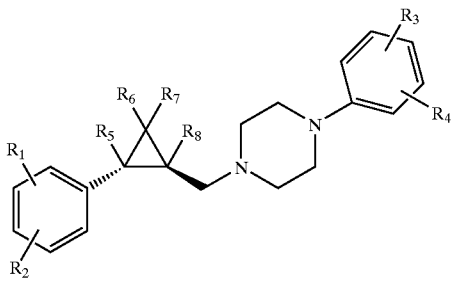

Vb wherein $R_1$ and $R_2$ independently represent hydrogen, halogen, $C_1$–$C_6$ alkyl, $C_1$–$C_6$ alkoxy, $C_1$–$C_4$ alkylthio, hydroxy, amino, mono- or di($C_1$–$C_6$)alkylamino, cyano, nitro, perfluoro($C_1$–$C_6$)alkyl or perfluoro($C_1$–$C_6$)alkoxy;

$R_3$ and $R_4$ are the same or different and represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$) alkylamino, cyano, nitro, perfluoro($C_1$–$C_6$)alkyl or perfluoro($C_1$–$C_6$)alkoxy; and $R_5$, $R_6$, $R_7$, and $R_8$ are the same or different and represent hydrogen or $C_1$–$C_3$ alkyl.

Preferred compounds of Formula Vb are those where $R_1$ and $R_2$ independently represent hydrogen, halogen, $C_1$–$C_6$ alkoxy, $C_1$–$C_4$ alkylthio, hydroxy, amino, mono- or di($C_1$–$C_6$)alkylamino, cyano, nitro or perfluoro($C_1$–$C_6$) alkoxy. More preferred compounds of Formula Vb are those where $R_5$, $R_6$, $R_7$, and $R_8$ are hydrogen or methyl. In these preferred compounds of Formula Vb, $R_5$ and $R_8$ are tsrans to each other.

Other more preferred compounds of Formula Vb are those where $R_3$ is hydrogen, halogen, $C_1$–$C_3$ alkyl, or $C_1$–$C_3$ alkoxy. Particularly preferred compounds of Formula Vb are those where $R_4$ is hydrogen, halogen, $C_1$–$C_3$ alkyl, or $C_1$–$C_3$ alkoxy and $R_3$ is hydrogen, halogen, $C_1$–$C_3$ alkyl, or $C_1$–$C_3$ alkoxy.

Other preferred compounds of Formula Vb are those where $R_3$ represents hydrogen, chloro, or methyl. Still other preferred compounds of Formula Vb are those where $R_4$ represents hydrogen, bromo chloro, methyl, nitro, or amino. Particularly preferred compounds of Formula Vb are those wherein $R_3$ represents hydrogen, chloro, or methyl, and $R_4$ represents hydrogen, bromo chloro, methyl, nitro, or amino.

In still other preferred compounds of Formula Vb, one of $R_1$ and $R_2$ may be halogen, preferably in the para position on the phenyl ring, while the other is hydrogen. In these preferred compounds $R_3$ and $R_4$ are preferably in the para and one of the ortho, i.e., the 4 and 2) positions with respect to the point of attachment to the phenyl ring and are hydrogen, halogen or $C_1$–$C_3$ alkyl, provided that at least one of $R_3$ and $R_4$ is not hydrogen.

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table 1 and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

Where a compound exists in various tautomeric forms, the invention is not limited to any one of the specific tautomers. The invention includes all tautomeric forms of a compound.

By "$C_1$–$C_6$ alkyl" or "lower alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$–$C_6$ alkyl groups are methyl, ethyl, propyl, butyl, cyclopropyl and cyclopropylmethyl.

By "$C_1$–$C_6$ alkoxy" or "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. Preferred alkoxy groups herein are $C_1$–$C_4$ alkoxy groups.

Preferred perfluoro($C_1$–$C_6$)alkyl groups of the invention are trifluoromethyl groups. Preferred perfluoro($C_1$–$C_6$)alkoxy groups of the invention are trifluoroalkoxy groups.

By the term "halogen" in the present invention is meant fluorine, bromine, chlorine, and iodine.

By aryl is meant an aromatic carbocyclic group having one ring (e.g., phenyl), or two rings (e.g., biphenyl). Such groups may be mono-, di-, or trisubstituted. Suitable substituents include, e.g., halogen, lower alkyl, lower alkoxy, lower alkylthio, trifluoromethyl, lower acyloxy, aryl, heteroaryl, and hydroxy.

By heteroaryl (aromatic heterocycle) in the present invention is meant one or more aromatic ring systems of 5-, 6-, or 7-membered rings containing at least one and up to four hetero atoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, naphthyridinyl, benzimidazolyl, and benzoxazolyl.

Representative compounds of the invention are shown in Table 1.

TABLE 1

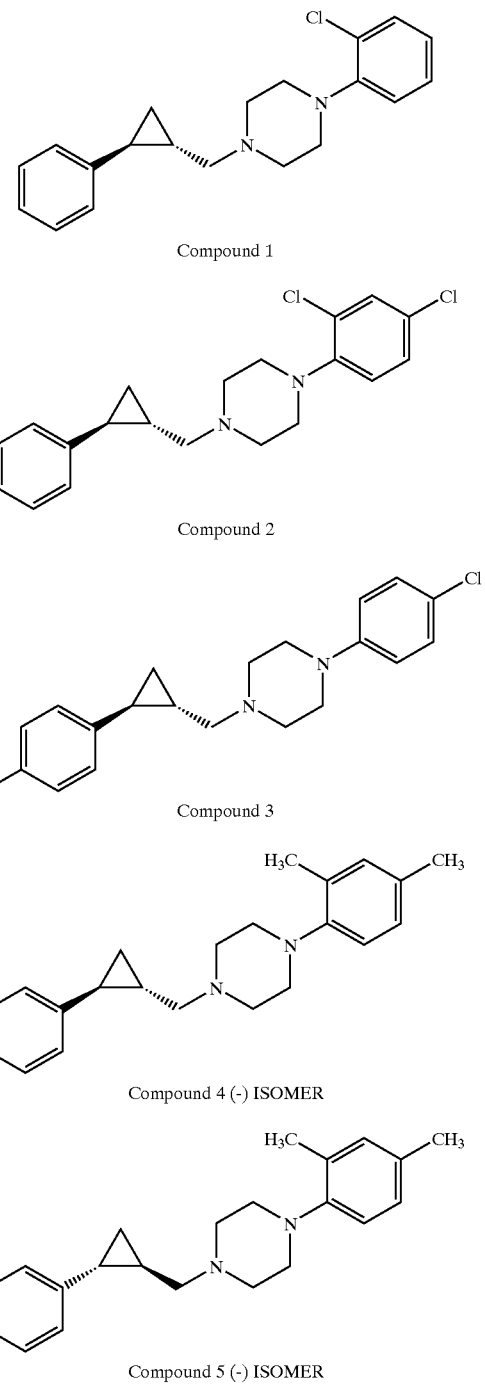

Compound 1

Compound 2

Compound 3

Compound 4 (-) ISOMER

Compound 5 (-) ISOMER

Compounds having this skeleton are preferred.

The invention also pertains to the use of compounds of general Formula I in the treatment of neuropsychological disorders. The interaction of compounds of the invention with dopamine receptors is shown in the examples. This interaction results in the pharmacological activity of these compounds.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A representative synthesis of the compounds of the invention is presented in Scheme I. Those having skill in the art will recognize that the starting materials may be varied and additional steps employed to produce compounds encompassed by the present invention.

yloxytris(dimethylamino)phosphonium hexafluorophosphate (BOP) or the like. Thereafter, compounds of Formula Ia may be prepared by reduction of IX with an appropriate reducing agent such as alane ($AlH_3$), borane ($BH_3$) or lithium aluminum hydride. Compounds of Formula I can likewise be prepared starting with piperazine VIII. Thus, piperazine VIII can be alkylated with a suitable alkylating agent that allows for subsequent coupling with acid VII. Coupling may be carried out with a derivative of acid VII such as, for example, a reduced form of the acid, i.e., an alcohol or aldehyde.

The compounds of general structure VI, VII, and VIII are either commercially available, known, or capable of being prepared by the methods known in the art. Where they are not commercially available, the compounds of general structure VI, VII and VIII may be prepared by procedures analogous to those described in literature. Those having skill in the art will recognize that the starting material may be varied and additional steps employed to produce compounds encompassed by the present invention.

The enantiomers of trans-2-phenylcyclopropane carboxylic acid can be prepared using the method of Overberger (Macromolecules, 4, 718 (1971)).

Scheme 1

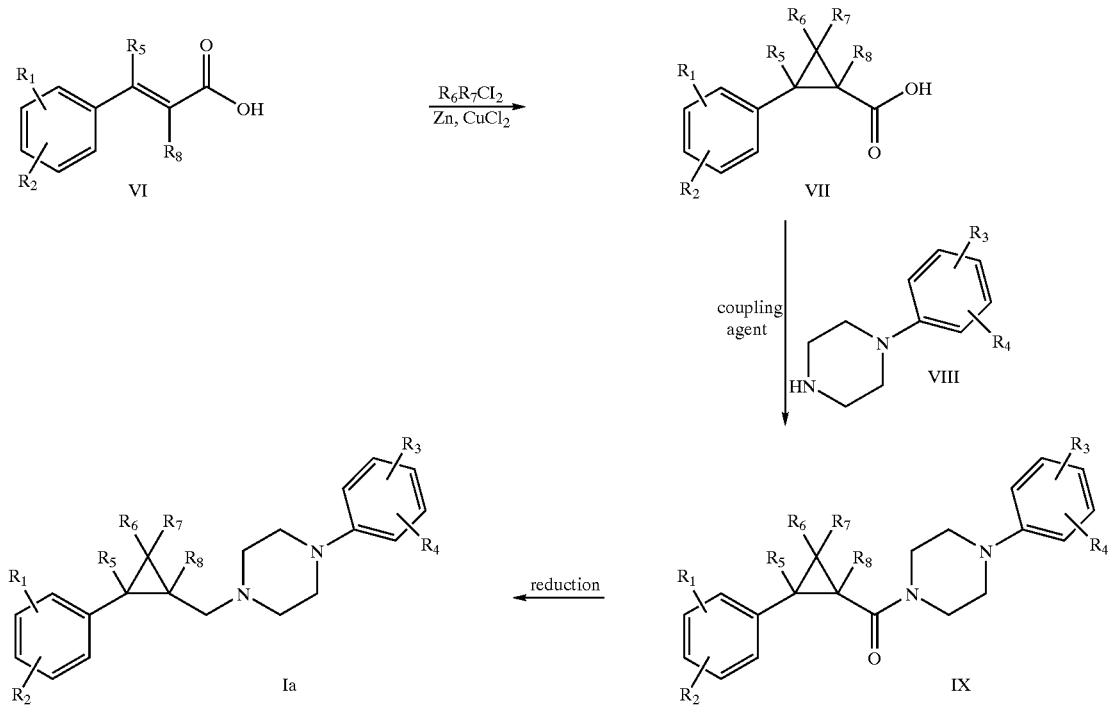

wherein $R_1$, $R_2$, $R_3$, $R_4$, $R_5$, $R_6$, $R_7$, and $R_8$ are as defined above for Formula I.

As shown, a 2-arylcyclopropanecarboxylic acid VII is prepared from a cinnamic acid VI through exposure to an appropriately substituted methylene iodide ($R_6R_7CI_2$) and zinc-copper couple. Variations of this procedure (the Simmons-Smith reaction) are well known in the literature (see Organic Reactions, Vol. 20, pages 1–131, 1982). Carboxylic acid VII is then condensed with an appropriately substituted 1-phenylpiperazine (VIII) in the presence of a coupling agent to provide a cyclopropylcarboxamide IX. Suitable coupling agents include carbonyl diimidazole (CDI), dicyclohexylcarbodiimide (DCC), benzotriazol-1-

Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, the need for such protecting groups will be apparent to those skilled in the art of organic synthesis as well as the conditions necessary to attach and remove such groups.

The disclosures in this application of all articles and references, including patents, are incorporated herein by reference.

EXAMPLE 1 trans 2-(4-chlorophenyl)cyclopropanecarboxylic acid

A mixture of zinc dust (6.54 g, 0.1 mole) and cuprous chloride (1 g, 0.01 mole) in methylene chloride (30 mL) is stirred and heated to reflux under a nitrogen atmosphere for 30 min. After the mixture is cooled to room temperature, methylene iodide (13.4 g, 0.05 mole) is added to the mixture which is then refluxed for an additional hour. After cooling to 0° C., trans-4-chlorocinnamic acid (9.1 g) is added. The reaction is allowed to warm to room temperature over 2 hours and then refluxed for 3 days. The reaction is quenched at 0° C. by the addition of 30 ml of diethyl ether and 30 ml of ice cold 10% $H_2SO_4$ solution. The mixture is filtered washed with ether. The organic layer is dried over $MgSO_4$ and concentrated to provide the desired product as a white solid. $^1$H NMR (CDCl$_3$) 7.25 (d, J=7 Hz, 2H), 7.05 (d, J=7 Hz, 2H), 2.58 (m, 1H), 1.85 (m, 1H), 1.65 (m, 1H), 1.37 (m, 1H).

EXAMPLE 2

1-(4-chlorophenyl)-4-(trans-2-[4-chlorophenyl] cyclopropyl)carbonylpiperazine

To a solution of trans 2-(4-chlorophenyl) cyclopropanecarboxyxlic acid (80 mg, 0.4 mmol) in 3 mL of dry methylene chloride is added diisopropylethylamine (0.15 ml), 1-(4-chlorophenyl)piperazine (110 mg) and benzotriazol-1-yloxytris(dimethylamino)phosphonium hexafluorophosphate (BOP, 0.2 g). The resulting mixture is stirred overnight, 10 mL of methylene chloride is added and the solution washed with water (2×10 mL). The organic layer is dried over MgSO$_4$ and concentrated. The resulting material is purified by flash chromatography eluting with 30% EtOAc/hexane to provide the desired amide as a yellow oil (70 mg, 39%) $^1$H NMR (CDCl$_3$) 7.2 (m, 4H), 7.03 (d, J=7 Hz, 2H), 6.83 (d, J=7 Hz, 2H), 3.8 (m, 4H), 3.18 (m, 4H), 2.50 (m, 1H), 1.95 (m, 1H), 1.62 (m, 1H), 1.25 (m, 1H).

EXAMPLE 3

1-(4-chlorophenyl)-4-(trans-2-[4-chlorophenyl] cyclopropyl)methylpiperazine

To a solution of 1-(4-chlorophenyl)-4-([trans-2-phenyl] cyclopropyl)carbonylpiperazine (70 mg) in tetrahydrofuran (3 mL) is added a solution of alane (1 M, 0.6 mL) in tetrahydrofuran. The reaction is stirred at room temperature for 2 hr, concentrated, diluted with ethyl acetate and washed with iN NaOH solution and water. The resulting organic layer is dried over MgSO$_4$ and concentrated. Purification by radial chromatography eluting with 2% methanol/methylene chloride provides 30 mg of the product as a white solid (Compound 3). $^1$H NMR (CDCl$_3$) 7.2 (m, 4H), 6.97 (d, J=7 Hz, 2H), 6.82 (d, J=7 Hz, 2H), 3.18 (M, 4H), 2.70 (m, 4H), 2.63 (dd, J=7, 5 Hz,1H), 2.4 (m, 1H), 1.65 (m, 1H), 1.22 (m, 1H), 0.9 (m, 2H). The fumarate salt (Compound 3A) is prepared in methanol and crystallized from ethyl acetate. m.p. 111–113° C.

EXAMPLE 4

The following compounds are prepared essentially according to the procedures set forth above.

(a) 1-(2-methylphenyl)-4-(trans-2-phenylcyclopropyl) methylpiperazine hydrobromide (Compound 6).
(b) 1-(2,4-dimethylphenyl)-4-(trans-2-phenylcyclopropyl) methylpiperazine hydrobromide (Compound 7).
(c) (S,S) 1-(2,4-dimethylphenyl)-4-(trans-2-phenylcyclopropyl)methylpiperazine hydrobromide (Compound 4, m.p. 224–225° C.)
(d) (R,R) 1-(2,4-dimethylphenyl)-4-(trans-2-phenylcyclopropyl)methylpiperazine hydrobromide (Compound 5, m.p. 205–206° C.).
(e) 1-(2-methyl-4-nitrophenyl)-4-(trans-2-phenylcyclopropyl)methylpiperazine hydrobromide (m.p. 197–198° C.) (Compound 8).
(f) 1-(2-methyl-4-aminophenyl)-4-(trans-2-phenylcyclopropyl)methylpiperazine hydrobromide (m.p. 284–285° C.) (Compound 9).
(g) 1-(2-methyl-4-bromophenyl)-4-(trans-2-phenylcyclopropyl)methylpiperazine hydrobromide (m.p. 182–183° C.) (Compound 10).
(h) 1-(4-chlorophenyl)-4-(trans-2-phenylcyclopropyl) methylpiperazine hydrobromide (m.p. 229–231° C.) (Compound 11)
(i) 1-(2,4-dichlorophenyl)-4-(trans-2-phenylcyclopropyl) methylpiperazine hydrobromide (Compound 2, m.p. 206–207° C.)
(j) 1-(2-chlorophenyl)-4-(trans-2-phenylcyclopropyl) methylpiperazine hydrobromide (Compound 1, m.p. 201–203° C.)

EXAMPLE 5

The pharmaceutical utility of compounds of this invention is indicated by the following assays for dopamine receptor subtype affinity.

Determination of $D_2$ and $D_4$ Receptor Binding Activity

Pellets of COS cells containing recombinantly produced $D_2$ or $D_4$ receptors from human are used for the assays. The sample is homogenized in 100 volumes (w/vol) of 0.05 M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:2 C (wt/vol) in 0.05 M Tris HCl buffer containing 100 mM NaCl.

Incubations are carried out at 48° C. and contain 0.4 ml of tissue sample, 0.5 nM $^3$H-YM 09151-2 and the compound of interest in a total incubation of 1.0 ml. Nonspecific binding is defined as that binding found in the presence of 1 mM spiperone; without further additions, nonspecific binding is less than 20% of total binding. The binding characteristics of examples of this patent for the $D_2$ and $D_4$ receptor subtypes are shown in Table 2.

TABLE 2

| Compound Number | $D_4$ $K_i$ (nM) | $D_2$ $K_i$ (nM) |
| --- | --- | --- |
| 1 | 8 | 7 |
| 2 | 8 | 90 |
| 3 | 8 | 523 |
| 4 | 2 | 75 |
| 5 | 10 | 51 |

The binding constants of compounds of Formula I for the $D_4$ receptor, expressed in nM, generally range from about 0.1 nanomolar (nM) to about 50 nanomolar (nM).

Preferably, such compounds have binding constraints of from about 0.1 to 10 nM. These compounds preferably have binding constants for the $D_2$ receptor of at least about 50 nM although compounds having lower $D_2$ binding constants may be used, although somewhat less preferably. Thus, the compounds of the invention are generally at least about 5 time more selective for the $D_4$ receptor than the $D_2$ receptor. Preferably, these compounds are at least 10, and more preferably at least 15–50, times more selective for the $D_4$ receptor than the $D_2$ receptor.

EXAMPLE 6

Preparation of Radiolabeled Probe Compounds of the Invention

The compounds of the invention are prepared as radiolabeled probes by carrying out their synthesis using precursors comprising at least one atom that is a radioisotope. Thus, the product is a compound of the invention that is comprised of at least 1 radioactive atom. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 7

Receptor Autoradiography

Receptor autoradiography (receptor mapping) is carried out in vitro using radiolabeled compounds of the invention (prepared as described in Example 6) as described by Kuhar in sections 8.1.1 to 8.1.9 of Current Protocols in Pharmacology (1998) John Wiley & Sons, New York and by Kuhar et al. in Annu. Rev. Neurosci, 1986, vol. 9, pages 27–59.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method for the treatment of schizophrenia comprising administering to a patient in need of such treatment an effective amount of (a) a compound of the formula:

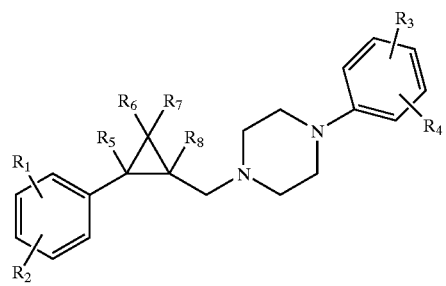

or (b) a pharmaceutically acceptable addition salt thereof wherein:

$R_1$ and $R_2$ independently represent hydrogen, halogen, $C_1$–$C_3$ alkyl, $C_1$–$C_4$ alkoxy, $C_1$–$C_4$ alkylthio, hydroxy, amino, mono- or di($C_1$–$C_6$)alkylamino, cyano, nitro, perfluoro($C_1$–$C_6$)alkyl or perfluoro ($C_1$–$C_6$) alkoxy;

$R_3$ and $R_4$ are the same or different and represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$)alkylamino, cyano, nitro, perfluoro ($C_1$–$C_6$)alkyl or perfluoro($C_1$–$C_6$)alkoxy; and $R_5$, $R_6$, $R_7$, and $R_8$ are the same or different and represent hydrogen or $C_1$–$C_3$ alkyl.

2. A method according to claim 1 wherein $R_1$ and $R_2$ are both hydrogen.

3. A method according to claim 1 wherein $R_1$ and $R_2$ are independently hydrogen, halogen, methyl, or ethyl, wherein at least one of $R_1$ and $R_2$ is not hydrogen.

4. A method according to claim 3, wherein $R_5$, $R_6$, $R_7$, and $R_8$ are hydrogen or methyl.

5. A method according to claim 4, wherein $R_5$ and $R_8$ are trans to each other.

6. A method for the treatment of schizophrenia comprising administering to a patient in need of such treatment an effective amount of (a) a compound of the formula

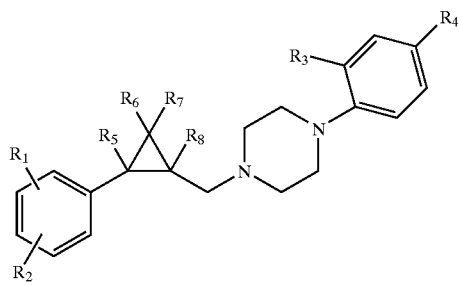

or (b) a pharmaceutically acceptable salt thereof wherein:

$R_1$ and $R_2$ independently represent hydrogen, halogen, $C_1$–$C_6$ alkyl, $C_1$–$C_6$ alkoxy, $C_1$–$C_4$ alkylthio, hydroxy, amino, mono- or di($C_1$–$C_6$)alkylamino, cyano, nitro, perfluoro($C_1$–$C_6$)alkyl or perfluoro ($C_1$–$C_6$) alkoxy;

$R_3$ and $R_4$ are the same or different and represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$)alkylamino, cyano, nitro, perfluoro ($C_1$–$C_6$)alkyl or perfluoro($C_1$–$C_6$)alkoxy; and R$_5$, R$_6$, R$_7$, and R$_8$ are the same or different and represent hydrogen or C$_1$–C$_3$ alkyl.

7. A method according to claim 6, wherein R$_1$ and R$_2$ are independently hydrogen or C$_1$–C$_6$ alkyl, provided that at least one of R$_1$ and R$_2$ is not hydrogen.

8. A method according to claim 7, wherein R$_5$, R$_6$, R$_7$, and R$_8$ are hydrogen or methyl.

9. A method according to claim 8, wherein R$_5$ and R$_8$ are trans to each other.

10. A method according to claim 6 wherein
R$_3$ represents hydrogen, chloro, or methyl; and
R$_4$ represents hydrogen, bromo chloro, methyl, nitro, or amino.

11. A method for the treatment of schizophrenia comprising administering to a patient in need of such treatment an effective amount of
(a) a compound of the formula

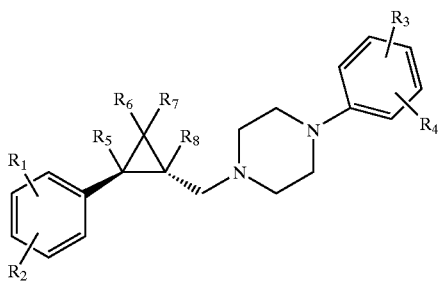

or
(b) a pharmaceutically acceptable salt thereof wherein:
R$_1$ and R$_2$ independently represent hydrogen, halogen, C$_1$–C$_6$ alkyl, C$_1$–C$_6$ alkoxy, C$_1$–C$_4$ alkylthio, hydroxy, amino, mono- or di(C$_1$–C$_6$)alkylamino, cyano, nitro, perfluoro(C$_1$–C$_6$)alkyl or perfluoro (C$_1$–C$_6$) alkoxy;
R$_3$ and R$_4$ are the same or different and represent hydrogen, halogen, C$_1$–C$_6$ alkyl, C$_1$–C$_4$ alkoxy, C$_1$–C$_4$ alkylthio, hydroxy, amino, mono- or di(C$_1$–C$_6$)alkylamino, cyano, nitro, perfluoro (C$_1$–C$_6$)alkyl or perfluoro(C$_1$–C$_6$)alkoxy; and
R$_5$, R$_6$, R$_7$, and R$_8$ are the same or different and represent hydrogen or C$_1$–C$_3$ alkyl.

12. A method for the treatment of mania, dementia, depression, anxiety, obsessive compulsive disorder, substance abuse, Parkinson-like motor disorder or a motion disorder related to the use of a neuroleptic agent comprising administering to a patient in need of such treatment an effective amount of
(a) a compound of the formula:

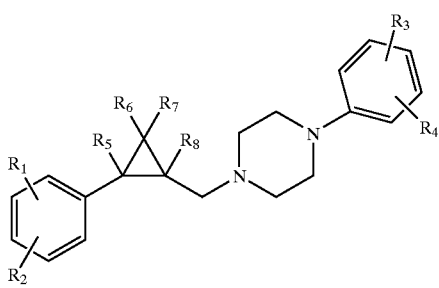

or
(b) a pharmaceutically acceptable addition salt thereof wherein:

R$_1$ and R$_2$ independently represent hydrogen, halogen, C$_1$–C$_3$ alkyl, C$_1$–C$_4$ alkoxy, C$_1$–C$_4$ alkylthio, hydroxy, amino, mono- or di(C$_1$–C$_6$)alkylamino, cyano, nitro, perfluoro(C$_1$–C$_6$)alkyl or perfluoro (C$_1$–C$_6$) alkoxy;
R$_3$ and R$_4$ are the same or different and represent hydrogen, halogen, C$_1$–C$_6$ alkyl, C$_1$–C$_4$ alkoxy, C$_1$–C$_4$ alkylthio, hydroxy, amino, mono- or di(C$_1$–C$_6$)alkylamino, cyano, nitro, perfluoro (C$_1$–C$_6$)alkyl or perfluoro(C$_1$–C$_6$)alkoxy; and
R$_5$, R$_6$, R$_7$, and R$_8$ are the same or different and represent hydrogen or C$_1$–C$_3$ alkyl.

13. A method according to claim 12 wherein R$_1$ and R$_2$ are both hydrogen.

14. A method according to claim 12 wherein R$_1$ and R$_2$ are independently hydrogen, halogen, methyl, or ethyl, wherein at least one of R$_1$ and R$_2$ is not hydrogen.

15. A method according to claim 14, wherein R$_5$, R$_6$, R$_7$, and R$_8$ are hydrogen or methyl.

16. A method according to claim 15, wherein R$_5$ and R$_8$ are trans to each other.

17. A method for the treatment of schizophrenia comprising administering to a patient in need of such treatment an effective amount of
(a) a compound of the formula

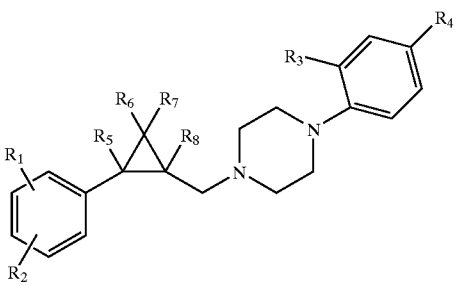

or
(b) a pharmaceutically acceptable salt thereof wherein:
R$_1$ and R$_2$ independently represent hydrogen, halogen, C$_1$–C$_6$ alkyl, C$_1$–C$_6$ alkoxy, C$_1$–C$_4$ alkylthio, hydroxy, amino, mono- or di(C$_1$–C$_6$)alkylamino, cyano, nitro, perfluoro(C$_1$–C$_6$)alkyl or perfluoro (C$_1$–C$_6$) alkoxy;
R$_3$ and R$_4$ are the same or different and represent hydrogen, halogen, C$_1$–C$_6$ alkyl, C$_1$–C$_4$ alkoxy, C$_1$–C$_4$ alkylthio, hydroxy, amino, mono- or di(C$_1$–C$_6$)alkylamino, cyano, nitro, perfluoro (C$_1$–C$_6$)alkyl or perfluoro(C$_1$–C$_6$)alkoxy; and
R$_5$, R$_6$, R$_7$, and R$_8$ are the same or different and represent hydrogen or C$_1$–C$_3$ alkyl.

18. A method according to claim 17, wherein R$_1$ and R$_2$ are independently hydrogen or C$_1$–C$_6$ alkyl, provided that at least one of R$_1$ and R$_2$ is not hydrogen.

19. A method according to claim 18, wherein R$_5$, R$_6$, R$_7$, and R$_8$ are hydrogen or methyl.

20. A method according to claim 19, wherein R$_5$ and R$_8$ are trans to each other.

21. A method according to claim 17 wherein
R$_3$ represents hydrogen, chloro, or methyl; and
R$_4$ represents hydrogen, bromo chloro, methyl, nitro, or amino.

22. A method for the treatment of mania, dementia, depression, anxiety, obsessive compulsive disorder, substance abuse, Parkinson-like motor disorder or a motion disorder related to the use of a neuroleptic agent comprising administering to a patient in need of such treatment an effective amount of (a) a compound of the formula

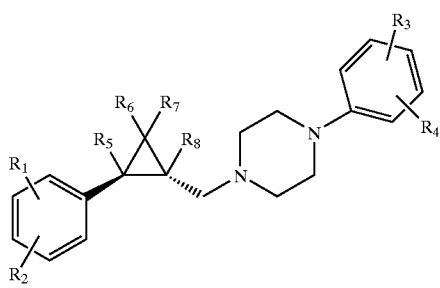

or (b) a pharmaceutically acceptable salt thereof wherein:
  $R_1$ and $R_2$ independently represent hydrogen, halogen, $C_1$–$C_6$ alkyl, $C_1$–$C_6$ alkoxy, $C_1$–$C_4$ alkylthio, hydroxy, amino, mono- or di($C_1$–$C_6$)alkylamino, cyano, nitro, perfluoro($C_1$–$C_6$)alkyl or perfluoro($C_1$–$C_6$) alkoxy;
  $R_3$ and $R_4$ are the same or different and represent hydrogen, halogen, $C_1$–$C_6$ alkyl, $C_1$–$C_4$ alkoxy, $C_1$–$C_4$ alkylthio, hydroxy, amino, mono- or di($C_1$–$C_6$)alkylamino, cyano, nitro, perfluoro($C_1$–$C_6$)alkyl or perfluoro($C_1$–$C_6$)alkoxy; and
  $R_5$, $R_6$, $R_7$, and $R_8$ are the same or different and represent hydrogen or $C_1$–$C_3$ alkyl.

* * * * *